United States Patent
Hill et al.

(10) Patent No.: US 7,184,829 B2
(45) Date of Patent: *Feb. 27, 2007

(54) METHOD AND SYSTEM FOR NERVE STIMULATION PRIOR TO AND DURING A MEDICAL PROCEDURE

(75) Inventors: Michael R. S. Hill, Minneapolis, MN (US); Scott E. Jahns, Hudson, WI (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 141 days.

This patent is subject to a terminal disclaimer.

(21) Appl. No.: 10/768,999

(22) Filed: Jan. 30, 2004

(65) Prior Publication Data

US 2004/0186517 A1 Sep. 23, 2004

Related U.S. Application Data

(63) Continuation of application No. 10/207,725, filed on Jul. 29, 2002, now Pat. No. 6,718,208, which is a continuation of application No. 09/670,441, filed on Sep. 26, 2000, now Pat. No. 6,449,507, which is a continuation-in-part of application No. 09/433,323, filed on Nov. 3, 1999, now Pat. No. 6,266,564, which is a continuation of application No. 09/070,506, filed on Apr. 30, 1998, now Pat. No. 6,006,134, which is a continuation-in-part of application No. 08/640,013, filed on Apr. 30, 1996, now abandoned.

(51) Int. Cl.
*A61N 1/362* (2006.01)

(52) U.S. Cl. .................. 607/2; 607/3; 607/9

(58) Field of Classification Search .............. 607/2–3, 607/9–10; 128/897–898
See application file for complete search history.

(56) References Cited

U.S. PATENT DOCUMENTS 3,614,995 A  10/1971  Probert et al.

(Continued)

FOREIGN PATENT DOCUMENTS

AU  9890156  3/1999

(Continued)

OTHER PUBLICATIONS

Coronary Artery Surgery With Induced Temporary Asystole and Intermittent Ventricular Pacing: An Experimental Study/R. Khanna and H.C. Cullen/Cardiovascular Surgery/Apr. 1996, vol. 4 No. 2 pp. 231-236.

(Continued)

*Primary Examiner*—Carl Layno
(74) *Attorney, Agent, or Firm*—Michael Best & Friedrich LLP

(57) ABSTRACT

A method of performing a medical procedure, such as surgery, is provided. A nerve is stimulated in order to adjust the beating of the heart to a first condition, such as a stopped or slowed condition. The medical procedure is performed on the heart or another organ. The stimulation of the nerve is stopped in order to adjust the beating of the heart to a second condition, such as a beating condition. The heart itself may also be stimulated to a beating condition, such as by pacing. The stimulation of the nerve may be continued in order to allow the medical procedure to be continued. Systems and devices for performing the medical procedure are also provided.

46 Claims, 4 Drawing Sheets

U.S. PATENT DOCUMENTS

| | | | |
|---|---|---|---|
| 3,804,098 A | 4/1974 | Friedman | |
| 3,937,226 A | 2/1976 | Funke | 128/419 D |
| 4,088,138 A | 5/1978 | Diack et al. | |
| 4,088,140 A | 5/1978 | Rockland et al. | 128/419 PG |
| 4,161,952 A | 7/1979 | Kinney et al. | |
| 4,176,660 A | 12/1979 | Mylrea et al. | |
| 4,198,963 A | 4/1980 | Barkalow et al. | |
| 4,303,075 A | 12/1981 | Heilman et al. | 128/419 PG |
| 4,304,239 A | 12/1981 | Perlin | 128/642 |
| 4,321,929 A | 3/1982 | Lemelson et al. | |
| 4,332,259 A | 6/1982 | McCorkle, Jr. | 128/786 |
| 4,351,330 A | 9/1982 | Scarberry | |
| 4,354,497 A | 10/1982 | Kahn | 128/419 D |
| 4,458,677 A | 7/1984 | McCorkle, Jr. | 128/786 |
| 4,548,203 A | 10/1985 | Tacker, Jr. et al. | 128/419 D |
| 4,574,807 A | 3/1986 | Hewson et al. | |
| 4,603,705 A | 8/1986 | Speicher et al. | |
| 4,640,298 A | 2/1987 | Pless et al. | 128/784 |
| 4,671,295 A | 6/1987 | Abrams et al. | |
| 4,715,367 A | 12/1987 | Crossley | |
| 4,722,347 A | 2/1988 | Abrams et al. | |
| 4,753,244 A | 6/1988 | Landymore et al. | |
| 4,919,147 A | 4/1990 | Reinhardt et al. | |
| 4,928,688 A | 5/1990 | Mower | 128/419 PG |
| 4,931,464 A | 6/1990 | Grover et al. | |
| 4,952,586 A | 8/1990 | Morris et al. | |
| 4,960,133 A | 10/1990 | Hewson | 128/784 |
| 5,003,991 A | 4/1991 | Takayama et al. | |
| 5,007,893 A | 4/1991 | Row | |
| 5,014,698 A | 5/1991 | Cohen | 128/419 D |
| 5,024,228 A | 6/1991 | Goldstone et al. | |
| 5,025,807 A | 6/1991 | Zabara | |
| 5,036,848 A | 8/1991 | Hewson | |
| 5,044,367 A | 9/1991 | Endres et al. | 128/419 R |
| 5,050,600 A | 9/1991 | Parks | |
| 5,052,390 A | 10/1991 | Hewson | 128/419 D |
| 5,056,519 A | 10/1991 | Vince | 128/419 G |
| 5,056,532 A | 10/1991 | Hull et al. | 128/785 |
| 5,117,822 A | 6/1992 | Laghi | |
| 5,117,828 A | 6/1992 | Metzger et al. | |
| 5,125,406 A | 6/1992 | Goldstone et al. | |
| 5,127,407 A | 7/1992 | Tan | |
| 5,129,392 A | 7/1992 | Bardy et al. | 128/419 D |
| 5,154,172 A | 10/1992 | Terry, Jr. et al. | |
| 5,156,149 A | 10/1992 | Hudrlik | |
| 5,156,151 A | 10/1992 | Imran | |
| 5,174,289 A | 12/1992 | Cohen | 128/419 PG |
| 5,178,149 A | 1/1993 | Imburgia et al. | |
| 5,179,950 A | 1/1993 | Stanislaw | |
| 5,179,952 A | 1/1993 | Buinevicius et al. | |
| 5,186,170 A | 2/1993 | Varrichio et al. | |
| 5,188,104 A | 2/1993 | Wernicke et al. | |
| 5,199,428 A | 4/1993 | Obel et al. | 128/419 C |
| 5,203,326 A | 4/1993 | Collins | 128/419 PG |
| 5,205,285 A | 4/1993 | Baker, Jr. | |
| 5,215,086 A | 6/1993 | Terry, Jr. et al. | |
| 5,231,988 A | 8/1993 | Wernicke et al. | |
| 5,235,980 A | 8/1993 | Varrichio et al. | |
| 5,243,980 A | 9/1993 | Mehra | 607/6 |
| 5,263,480 A | 11/1993 | Wernicke et al. | |
| 5,265,603 A | 11/1993 | Hudrlik | |
| 5,265,623 A | 11/1993 | Kroll et al. | |
| 5,267,560 A | 12/1993 | Cohen | 607/25 |
| 5,269,303 A | 12/1993 | Wernicke et al. | |
| 5,282,468 A | 2/1994 | Klepinski | |
| 5,284,146 A | 2/1994 | Czar et al. | |
| 5,292,338 A | 3/1994 | Bardy | 607/5 |
| 5,299,569 A | 4/1994 | Wernicke et al. | |
| 5,304,120 A | 4/1994 | Crandell et al. | |
| 5,304,206 A | 4/1994 | Baker, Jr. et al. | |
| 5,304,220 A | 4/1994 | Maginot | |
| 5,330,507 A | 7/1994 | Schwartz | 607/14 |
| 5,330,515 A | 7/1994 | Rutecki et al. | 607/46 |
| 5,334,221 A | 8/1994 | Bardy | 607/14 |
| 5,335,657 A | 8/1994 | Terry, Jr. et al. | |
| 5,354,318 A | 10/1994 | Taepke | 607/22 |
| 5,356,425 A | 10/1994 | Bardy et al. | 607/14 |
| 5,365,926 A | 11/1994 | Desai | |
| 5,379,765 A | 1/1995 | Kajiwara et al. | |
| 5,403,356 A | 4/1995 | Hill et al. | 607/14 |
| 5,411,529 A | 5/1995 | Hudrlik | |
| 5,417,713 A | 5/1995 | Cohen | |
| 5,456,254 A | 10/1995 | Pietroski et al. | |
| 5,458,625 A | 10/1995 | Kendall | |
| 5,476,485 A | 12/1995 | Weinberg et al. | |
| 5,501,702 A | 3/1996 | Plicchi et al. | 607/20 |
| 5,501,703 A | 3/1996 | Holsheimer et al. | 407/46 |
| 5,507,784 A | 4/1996 | Hill et al. | 607/14 |
| 5,514,161 A | 5/1996 | Limousin | 607/9 |
| 5,531,776 A | 7/1996 | Ward et al. | |
| 5,540,730 A | 7/1996 | Terry, Jr. et al. | 607/40 |
| 5,540,732 A | 7/1996 | Testerman | 607/42 |
| 5,549,655 A | 8/1996 | Erickson | 607/42 |
| 5,571,150 A | 11/1996 | Wernicke et al. | 607/72 |
| 5,578,061 A | 11/1996 | Stroetmann et al. | 607/4 |
| 5,584,867 A | 12/1996 | Limousin et al. | 607/9 |
| 5,611,350 A | 3/1997 | John | 128/731 |
| 5,620,468 A | 4/1997 | Mongeon et al. | 607/5 |
| 5,651,378 A | 7/1997 | Matheny et al. | 128/898 |
| 5,656,420 A | 8/1997 | Chien | |
| 5,662,689 A | 9/1997 | Elsberry et al. | |
| 5,668,117 A | 9/1997 | Shapiro | |
| 5,674,259 A | 10/1997 | Gray | 607/20 |
| 5,690,681 A | 11/1997 | Geddes et al. | 607/2 |
| 5,700,282 A | 12/1997 | Zabara | 607/9 |
| 5,707,400 A | 1/1998 | Terry, Jr. et al. | |
| 5,713,924 A | 2/1998 | Min et al. | |
| 5,713,929 A | 2/1998 | Hess et al. | |
| 5,720,768 A | 2/1998 | Verboven-Nelissen | 607/9 |
| 5,755,682 A | 5/1998 | Knudson et al. | |
| 5,782,874 A | 7/1998 | Loos | |
| 5,791,187 A | 8/1998 | Chang | |
| 5,792,187 A | 8/1998 | Adams | 607/5 |
| 5,792,203 A | 8/1998 | Schroeppel | 607/30 |
| 5,797,970 A | 8/1998 | Pouvreau | 607/9 |
| 5,799,661 A | 9/1998 | Boyd et al. | |
| 5,824,021 A | 10/1998 | Rise | |
| 5,836,994 A | 11/1998 | Bourgeois | 607/40 |
| 5,840,076 A | 11/1998 | Swanson et al. | |
| 5,846,263 A | 12/1998 | Peterson et al. | |
| 5,846,264 A | 12/1998 | Andersson et al. | |
| 5,874,420 A | 2/1999 | Pelleg | |
| 5,889,033 A | 3/1999 | Kaminski | |
| 5,893,881 A | 4/1999 | Elsberry et al. | |
| 5,893,882 A | 4/1999 | Peterson et al. | |
| 5,902,324 A | 5/1999 | Thompson et al. | 607/9 |
| 5,913,876 A | 6/1999 | Taylor et al. | 607/2 |
| 5,916,239 A | 6/1999 | Geddes et al. | 607/14 |
| 5,928,272 A | 7/1999 | Adkins et al. | 607/45 |
| 5,964,789 A | 10/1999 | Karsdon | 607/39 |
| 5,971,911 A | 10/1999 | Wilk | |
| 5,977,408 A | 11/1999 | Levin et al. | 562/622 |
| 5,995,872 A | 11/1999 | Bourgeois | |
| 5,998,386 A | 12/1999 | Feldman | 514/46 |
| 6,006,134 A | 12/1999 | Hill et al. | 607/9 |
| 6,007,559 A | 12/1999 | Arkans | |
| 6,014,588 A | 1/2000 | Fitz | |
| 6,042,538 A | 3/2000 | Puskas | |
| 6,043,273 A | 3/2000 | Duhaylongsod | 514/478 |
| 6,060,454 A | 5/2000 | Duhaylongsod | 514/26 |
| 6,073,048 A | 6/2000 | Kieval et al. | 607/17 |
| 6,087,394 A | 7/2000 | Duhaylongsod | 514/478 |
| 6,091,988 A | 7/2000 | Warman et al. | |
| 6,101,412 A | 8/2000 | Duhaylongsod | 607/2 |

| | | | |
|---|---|---|---|
| 6,103,722 A | 8/2000 | Schultz et al. | |
| 6,127,410 A | 10/2000 | Duhaylongsod | 514/478 |
| 6,141,589 A | 10/2000 | Duhaylongsod | 607/10 |
| 6,141,590 A | 10/2000 | Renirie et al. | 607/20 |
| 6,185,459 B1 | 2/2001 | Mehra et al. | |
| 6,221,851 B1 | 4/2001 | Feldman | 514/46 |
| 6,234,985 B1 | 5/2001 | Lurie et al. | |
| 6,253,108 B1 | 6/2001 | Rosborough et al. | |
| 6,266,564 B1 | 7/2001 | Hill et al. | |
| 6,272,380 B1 | 8/2001 | Warman et al. | |
| 6,299,564 B1 | 10/2001 | Gessler et al. | |
| 6,303,293 B1 | 10/2001 | Patterson et al. | |
| 6,304,777 B1 | 10/2001 | Ben-Haim et al. | |
| 6,381,499 B1 | 4/2002 | Taylor et al. | 607/118 |
| 6,414,018 B1 | 7/2002 | Duhaylongsod | |
| 6,429,217 B1 | 8/2002 | Puskas | |
| 6,442,429 B1 | 8/2002 | Hill et al. | |
| 6,447,443 B1 * | 9/2002 | Keogh et al. | 600/37 |
| 6,449,507 B1 | 9/2002 | Hill et al. | |
| 6,473,644 B1 | 10/2002 | Terry, Jr. et al. | 607/2 |
| 6,479,523 B1 * | 11/2002 | Puskas | 514/346 |
| 6,487,446 B1 | 11/2002 | Hill et al. | |
| 6,532,388 B1 * | 3/2003 | Hill et al. | 607/2 |
| 6,537,540 B1 | 3/2003 | Burstein et al. | 424/93.2 |
| 6,542,774 B2 | 4/2003 | Hill et al. | |
| 6,554,781 B1 | 4/2003 | Hill et al. | |
| 6,572,895 B2 | 6/2003 | Smith et al. | 424/529 |
| 6,587,719 B1 | 7/2003 | Barrett et al. | |
| 6,589,954 B1 | 7/2003 | Mavunkel et al. | 514/253 |
| 6,609,025 B2 | 8/2003 | Barrett et al. | |
| 6,622,038 B2 | 9/2003 | Barrett et al. | |
| 6,622,041 B2 | 9/2003 | Terry, Jr. et al. | |
| 6,622,047 B2 | 9/2003 | Barrett et al. | |
| 6,628,987 B1 | 9/2003 | Hill et al. | |
| 6,656,960 B2 | 12/2003 | Puskas | |
| 6,690,973 B2 | 2/2004 | Hill et al. | |
| 6,711,436 B1 | 3/2004 | Duhaylongsod | |
| 6,718,208 B2 * | 4/2004 | Hill et al. | 607/9 |
| 6,721,603 B2 | 4/2004 | Zabara et al. | |
| 6,735,471 B2 | 5/2004 | Hill et al. | |
| 6,738,667 B2 | 5/2004 | Deno et al. | |
| 6,778,854 B2 | 8/2004 | Puskas | |
| RE38,654 E | 11/2004 | Hill et al. | |
| RE38,705 E | 2/2005 | Hill et al. | |
| 6,904,318 B2 | 6/2005 | Hill et al. | |
| 6,912,419 B2 | 6/2005 | Hill et al. | |
| 2001/0049543 A1 | 12/2001 | Kroll | 607/28 |
| 2002/0072782 A1 | 6/2002 | Osorio et al. | |
| 2002/0198570 A1 | 12/2002 | Puskas | |
| 2002/0198571 A1 | 12/2002 | Puskas | |
| 2003/0045909 A1 | 3/2003 | Gross et al. | |
| 2003/0074039 A1 | 4/2003 | Puskas | |
| 2003/0216775 A1 | 11/2003 | Hill et al. | |
| 2003/0216790 A1 | 11/2003 | Hill et al. | |
| 2004/0024422 A1 | 2/2004 | Hill et al. | |
| 2004/0059383 A1 | 3/2004 | Puskas | |
| 2004/0111118 A1 | 6/2004 | Hill et al. | |
| 2004/0162584 A1 | 8/2004 | Hill et al. | |
| 2004/0172075 A1 | 9/2004 | Shafer et al. | |
| 2004/0186517 A1 | 9/2004 | Hill et al. | |
| 2004/0186531 A1 | 9/2004 | Jahns et al. | |
| 2004/0199209 A1 | 10/2004 | Hill et al. | |
| 2005/0096707 A1 | 5/2005 | Hill et al. | |
| 2005/0143412 A1 | 6/2005 | Puskas | |

FOREIGN PATENT DOCUMENTS

| | | |
|---|---|---|
| AU | 779255 | 6/2000 |
| CA | 2310183 | 5/1996 |
| CA | 2376903 | 6/2000 |
| DE | 28 11 325 | 9/1979 |
| EP | 0440111 | 8/1991 |
| EP | 0 589 252 | 9/1993 |
| EP | 0589252 | 3/1994 |
| EP | 0688579 | 12/1995 |
| EP | 1005337 | 6/2000 |
| EP | 1181947 | 2/2002 |
| JP | 2000-507363 | 8/1998 |
| JP | 2001-505980 | 6/2000 |
| MX | 2043 | 8/1998 |
| WO | WO 92/11064 | 9/1993 |
| WO | WO 97/40885 | 11/1997 |
| WO | WO 99/00057 | 1/1999 |
| WO | WO 99/07354 | 2/1999 |
| WO | WO 99/09971 | 3/1999 |
| WO | WO 99/09973 | 3/1999 |
| WO | WO 99/63926 | 12/1999 |
| WO | WO 00/01306 | 1/2000 |
| WO | WO01/00273 | 6/2000 |
| WO | WO 01/89526 | 11/2001 |
| WO | WO 00/09206 | 2/2002 |
| WO | WO 02/26320 | 4/2002 |

OTHER PUBLICATIONS

Editorial/Adrian R.M. Upton/PACE, Oct., Part II 1992 vol. 15 pp. 1543-1544.

Neural Effects On Sinus Rate and Atrioventricular Conduction Produced by Electrical Stimulation from a Transvenous Electrode Catheter in the Canine Right Pulmonary Artery/Terry B. Cooper, Gilbert R. Hageman, Thomas N. James, and Albert L. Waldo/ Circulation Research vol. 46, No. 1, Jan. 1980.

Selective Stimulation of Parasympathetic Nerve Fibers to the Human Sinoatrial Node/Mark D. Carlson, MD, MA; Alexander S. Geha, MD, MS; Jack Hsu, MD; Paul J. Martin, PhD; Matthew N. Levy, MD; Gretta Jacobs, MD; and Albert 1. Waldo, MD/Circulation—vol. 85, No. 4 pp. 1311-1317.

Controlled Intermittent Asysteole: Pharmacologic Potential of Vagal-Induced Asystole/Bradley L. Burkin, MD; John D. Puskas, MD; Jakob Vinten-Johansen, PhD; Steven T. Shearer, BS; and Robert A. Guyton, MD/The Society of Thoracic Surgeons—1998.

Controlled Ventricular Asystole With Surgeons—Actuated Pacing For Off-Pump Coronary Artery Bypass Grafting: A Proposed Surgical Method/Francis G. Duhaylongsod and William R. Burfeind, Jr./IBMCS Abstract—Jun. 25, 1998.

Age-Related Changes of Cardiac Control Function in Man: With special reference to heart rate control at rest and during exercise. /Iwao Sato, MD; Yasuhiro Hasegawa, MD; Norikazu Takahashi, MD; Yukio Hirata, MD; Katsuro Shimomura, MD; and Ken Hotta, PhD./ Journal of Gerontology, 1981, vol. 36, No. 5, pp. 564-572.

Cardiac Muscarinic Receptors Decrease with Age/Otto-Erich Brodde; Ulrich Konschak; Karin Becker; Florian Ruter; Ulrike Potter; Jens Jakubetz; Joachim Radke; and Hans-Reinhard Zerkowski/J. Clin. Invest. vol. 101, No. 2. Jan. 1998, 471-478.

Age-Dependent Changes in Cardiac Muscarinic Receptor Function in Healthy Volunteers/Ulrike Pller, MD; Gesine Nedelka, MD; Joachim Radke, MD; Klaus Poinicke, Ph.D.; and Otto-Erich Brodde, Pd.D./JACC vol. 29. No. 1 Jan. 1997: 187-93.

Age-Related Changes of Cardiac Parasympathetic Modulation After Vasovagal Syncope/Alfonso Lagi, MD; Simone Cencetti, MD; Lamberto Fattorini, MD; and Carlo Tamburini, MD/The American Journal of Cardiology vol. 83 Mar. 15, 1999.

Desensitization of the Cholinergic receptor at the sinoatrial cell of the kitten/Jose Jalife; Allan J. Hamilton, and Gordon K. Moe/1980 the American Physiological Society.

Sensitivity differences of SA and AV node to vagal stimulation: attenuation of vagal effects at SA node/Jerod M. Loeb; Daniel P. Dalton; and John M. Moran/1981 the American Physiological Society.

Vagal Nerve Monitoring: A Comparison of Techniques in a Canine Model/Mark A. Severtson; John P. Leonette; and Denise Jarocki/ The American Journal of Otology 18:398-400 1997.

The NIM-2 nerve integrity monitor in thyroid and parathyroid surgery/J. Barwell; J. Lytle; R. Page; and D. Wilkins/British Journal of Surgery 1997, 84, 854.

A New Method For Intraoperative Recurrent Laryngeal Nerve Monitoring/Richard W. Maloney, MD; Benjamin W. Murcek, DO; Kirk W. Steehler, DO; Dennis Sibly; Richard E. Maloney/ ENT Journal Jan. 1994.

Revision and Removal of Stimulating Electrodes Following Long-Term Therapy with the Vagus Nerve Stimulator/Jose Espinosa, MD; Mary T. Aiello, MA; and Dean K. Naritoku, MD/1999 by Elsevier Science Inc./Surg Neurol 1999:51:659-64.

Epilepsy, Vagal Nerve Stimulation by the NCP System, All-Cause Mortality, and Sudden, Unespected, Unexplained Death/J.F. Annegers; Sharon P. Coan; W.A. Hauser; and J. Leestma/Epilesia, vol. 41. No. 5. 2000.

Fade of cardiac responses during tonic vagal stimulation/Paul Martin, Matthew N. Levy, and Yasuo Matsuda/1982 the American Physiological Society.

Experiences in Minimally Invasive Cardiac Surgery—Techniques of Stabilization/Robert G. Matheny, MD/ presented by the Minneapolis Heart Institute Foundation Jun. 19-21, 1997.

Vagus Nerve Stimulation as a Method to Temporarily Slow or Arrest the Heart/Robert G. Matheny, MD; and Carl J. Shaar, PhD/1997 by The Society of Thoracic Surgeons.

Vagus Nerve Stimulation for Treatment of Partial Seizures: 1. A Controlled Study of Effect on Seizures/E. Ben-Menachem, R. Manon-Espaillat; R. Ristanovic; B.J. Wilder; H. Stefan; W. Mirza; W.B. Tarver; J.F. Wernicke; and First International Vagus Nerve Stimulation Study Group/Epilepsia, 35(3):616-626, 1994.

Vagus Nerve Stimulation for Treatment of Partial Seizures: 2. Safety, Side Effects, and Tolerability/R.E. Ramsay; B.M. Uthman; L.E. Augustinsson; A.R.M. Upton; D. Naritoku; J. Willis; T. Treig; G. Barolat; J.F. Wernicke; and First International Nerve Study Group/Epilepsia. 35(3) 627-636, 1994.

Vagus Nerve Stimulation for Treatment of Partial Seizures: 3. Long-Term Follow-Up On First 67 Patients Exiting a Controlled Study/R. George; M. Salinsky; R. Kuzniedky; W. Rosenfeld; D. Bergen; W.B. Tarver; J.F. Wernicke; and First International Nerve Stimulation Study Group/Epilepsia. 35(3):637-643, 1994.

Vagus Nerve Stimulation for the Control of Epilepsy/Epilepsia Journal of the International League Against Epilepsy/Proceedings of a Symposium held I conjunction with the American Epilepsy Society Annual Meeting Boston, MA Dec. 2, 1989.

Inflammatory Mediators and the Failing Heart: A Translational Approach/Abhinav Diwan, Tony Tran, Arunima Misra and Douglas L. Mann/Curr Mol Med. 2003: 3:161-82.

The Role of Tumor Necrosis Factor Alpha Blockade in the Treatment of Congestive Heart Failure/Lisman KA, Stetson SJ, Koerner MM, Farmer JA, Torre-Amione G./Congest Heart Fail. 2002; 8 (5):275-9.

The Importance of Tumor Necrosis Factor and Lipoproteins in the Pathogenesis of Chronic Heart Failure/Sharma R, Al-Nasser FO, adn Anker SD/Heart Fail Monit. 2001:2(2):42-7.

Cardiac Myocyte Necrosis Induced by Angiotensin II/Lip-Bun Tan, Jorge E. Jalil, Ruth Pick, Joseph S. Janicki and Karl T. Weber/ Circulation Research vol. 69, No. 5, Nov. 1991 pp. 1185-1195.

The Adrenergic Nervous System In Heart Failure/Michael R. Bristow, M.D./The New England Journal of Medicinevol. 311 No. 13 Sep. 27, 1984 pp. 850-851.

Negative Inotropic Effects of Cytokines on the Heart Mediated by Nitric Oxide/Mitchell S. Finkel, Carmine V. Oddis, Timothy D. Jacob, Simon C. Watkins, Brack G. Hattler and Richard L. Simmons/Science vol. 257 Jul. 17, 1992, pp. 387-389.

Immunoregulatory Feedback Between Interleukin-1 and Glucocorticoid Hormones/H. Besedovsky, A. Del Rey, E. Sorkin, and C. Dinarello/Science vol. 233 Aug. 8, 1986, pp. 652-654.

Role of vagus nerve signaling in CNI1493-mediated suppression of acute inflammation/L. Borovikova, S. Ivanova, D. Nardi, M. Zhang, H Yang, M. Ombrellino and K. Tracey/Elsevier Science B.V. Atuonomic Neuroscience: Basic and Clinical 85 (2000) 141-147.

Cellular Basis for the Negative Inotropic Effects of Tumor Necrosis Factor-α in the Adult Mamalian Heart/T. Yokoyama, L. Vaca, R. Rossen, W. Durante, P Hazarika and D. Mann/The Journal of Clinical Investigation, Inc./vol. 92, Nov. 1993, 2303-2312.

Cytokines and Cardiomyocyte Death/Kari J. Pulkki/ 1997 The Finnish Medical Society DUODECIM, Ann Med 29, 339-343.

Subdiaphragmatic vagotomy suppressed endotoxin-induced activation of hypothalamic corticotropin-releasing hormone neurons and ACTH secretion/R.P.A. Gaykema, I. Dukstra, and F.J.H. Tilders/ Endocrinologyvol. 136, No. 136, No. 10 pp. 4717-4720.

Interleukin 1 and tumor necrosis factor inhibit cardiac myocyte β-adrenergic responsiveness/T. Gulick, M.K. Chung, S.J. Pieper, L.G. Lange, and G.F. Schreiner/Proc. Natl. Acad. Sci vol. 86 pp. 6753-6757, Sep. 1989 Medical Sciences.

Mechanisms and Models In Heart Failure A Combinatorial Approach/D.L. Mann, MD/Circulation 1999; 100:999-1008.

Proteomics of heart disease/Em McGregor and M.J. Dunn/Human Molecular Genetis, vol. 12, Review Issue 2 2003 R135-R144.

Geriatric Cachexia: the role of cytokines[1,2] Shing—Shing Yeh and Michael W. Schuster/Am J. Clin Nutr 1999, 70:183-197.

Thermogenic and corticosterone response to intravenous cytokines (IL-1β and TNF-α) are attenuated by subdiaphragmatic vagotomy/ M. Fleshner, L.E. Goehler, B.A. Schwartz, M. McGorry, D. Martin, S.F. Maier, and L.R. Watkins/Journal of Neuroimmunology/ Elesevier Science B.V. 86 (1998) 134-141.

Implications of immune-to-brain communication for sickness and pain/L.R. Watkins and S.F. Maier/Proc. Natl. Acad. Sci vol. 96, pp. 7710-7713, Jul. 1999.

Loss of a gp130 Cardiac Muscle Cell Survival Pathway Is a Critical Event in the Onset of Heart Failure during Biomechanical Stress/H. Hirota, J. Chen, U.A.K. Betz, K. Rajewsky, Y. Gu, J. Ross, Jr., W. Muller and K. R. Chien/Cell. vol. 97 189-198 Apr. 16, 1999.

Vagus nerve stimulation attenuates the systemic inflammatory response to endotoxin/L. V. Borovikova, S. Ivanova, M. Zhang, H. Yang, G.I. Botchkina, L.R. Watkins, H. Wang, N. Abumrad, J.W. Eaton and K.J. Tracey/Nature vol. 405 May 25, 2000 pp. 458-462.

Efferent Vagal Fibre Stimulation Blunts Nuclear Factor-κB Activation and Protects Against Hypovolemic Hemorrhagic Shock/S. Guarini, Ph.D; D. Altavilla, Ph.D; MM Cainazzo, MD; D. Giuliani, Ph.D; A. Bigiani, Ph.D; H. Marini, MD; G. Squadrito, MD; L. Minutoli, MD; A. Bertolini, MD; R. Marini, Ph.D.; E.B. Adamo, MD; F.S. Venuti, MD; and F. Squadrito, MD/Circulation Mar. 4, 2003 pp. 1189-1194.

Myocardial extracellular matrix remodeling in transgenic mice overexpressing tumor necrosis factor α can be modulated by anti-tumor necrosis factor α therapy/Y. Y. Li; Y. Q. Feng; T. Kadokami; C.F. McTiernan; R. Draviam; S.C. Watkins; and A.M. Feldman/PNAS Nov. 7, 2000 vol. 97 No. 23 pp. 12746-12751.

Tumor Necrosis Factor Alpha-induced Apoptosis in Cardiac Myocytes Involvement of the Sphingolipid Signaling Cascade in Cardiac Cell Death/K.A. Krown; M. Trevor Page; C. Nguyen; D. Zechner; V. Gutierrez; K.L. Comstock; C.C. Glembotski; P. J.E. Quintana; and R.A. Sabbadini/J. Clin. Invest. vol. 98 No. 12, Dec. 1996, 2854-2865.

New Therapeutics For Chronic Heart Failure/D.L. Mann; A. Deswal; B. Bozkurt; and G. Torre-Amione/Annu. Rev. Med. 2002 53:59-74.

Tumor Necrosis Factor-α Provokes a Hypertrophic Growth Response in Adult Cardiac Myocytes/T. Yokoyama, MD; M. Nakano, MD, PhD; J.L. Bednarczyk, PhD; B.W. McIntyre, PhD; M. Entman, MD; D.L. Mann, MD/Circulation 1997; 95:1247-1252.

U.S. Appl. No. 09/980,421.

Agnew, William F., et al., Consideration for Safety with Chronically Implanted Nerve Electrodes, Epilepsia, 31(Supp. 2), 1990, pp. S27-S32, Reven Press, Ltd., New York.

Bell, et al., "Inotropic Responses of the Left Ventricle to Changes in Heart Rate in Anesthetized Rabbits," Can. J. Physiol. Pharmacol., 65:179-184.

Bennetti, F.J., Direct Coronary Surgery with Saphenous Vein Bypass Without Either Cardiopulmonary Bypass or Cardiac Arrest, J. Cardiovasc. Surg., 26:217-222.

Benetti, et al., "Use of Thoracoscopy and a Minimal Thoracotomy, in Mammary-Coronary Bypass to Left Anterior Descending Artery, Without Extracorporeal Circulation," J. Cardiovasc. Surg., 36:159-161.

Bilgutay, A., et al., "Vagal Tuning: A New Concept in the Treatment of Supraventricular Arrhythmias, Angina pectoris, and Heart failure," Jour. of Thorac. & Cardio. Surg., 1968, pp. 71-82.

Bluemel, K.M., et al., "Parasympathetic Postganglionic Pathways to the Sinoatrial Node," Am. Phys. Soc., 1990, pp. H1508.

Braunwald, E., et al., "Cartoid Sinus Nerve Stimulation in the Treatment of Angina Pectoris and Supraventricular Tachycardia," Western Jour. of Medicine, 1970, No. 112, Vol. 3, pp. 41-50.

Bufkin, B., et al., "Controlled Intermittent Asystole: Pharmacologic Potentiation of Vagal-Induced Asystole," Ann. Thorac. Surg. 1998; 66: 1185-90.

Declaration/Clarification of John D. Puskas, MD., dated Oct. 11, 2005, pp. 1-7.

Dimarco, J. P., M.D., et al., "Adenosine: Electrophysiologic Effects and Therapeutic Use for Terminating Paroxymal Supraventricular Tachycardia," therapy and Prevention arrhythmia, Circulation 68, No. 6, 1983, pp. 1254-1263.

Dipiro, J., et al., "Pharmacotherapy: A Pathophysiologic Approach," p. 153-157, 1989.

Fanning, et al., "Reoperative Coronary Bypass Grafting Without Cadiopulmonary Bypass," Ann. Thorac. Surg., 55:486-489.

Freilich, A., M.D., et al., "Adenosine and its Cardiovascular Effects, " American Heart Journal, vol. 123, No. 5, May 1992, pp. 1324-1328.

Gorman, Christine, et al., "How New Heart-Scanning Technology Could save Your Life," *Time* , Sep. 5, 2005, pp. 61 and 67.

Hageman, G.R., et al., "Direct and Reflex Cardiac Bradydysrhythmias from a Small Vagal Nerve Stimulations," Am. Heart J. 1975, Mar; 89: 338-48 (Abstract only).

Hammond, Edward J., et al., "Vagus Nerve Stimulation in Humans: Neurophysiological Studies and Electrophysiological Monitoring," Epilepsia, 31 Suppl. 2), 1990, pp. S51-S59, Raven Press, Ltd., New York.

Klassen, et al., "Coronary Venous Pressure and Flow: Effects of Vagal Stimulation, Aortic Occlusion, and Vasodilators," Can. J. Physiol. Pharmacol., 1984, 62:531-538.

Levy, M. et al., "Autonomic Control of Cardiac Pacemaker Activity and Atrioventricular Transmission," Journal of Applied Physiology, vol. 27 No. 4, Oct 1969.

Lockard, Joan S., et al., "Feasibility and Safety of Vagal Stimulation in Monkey Model," Epilepsia, 31 (Supp. 2), 1990, pp. S20-S26, Raven Press, Ltd., New York.

Mohiuddin, S. M., M.D., et al., "Safety of Different Dosages of Intravenous Adenosine Used in Conjunction with Diagnostic Myocardial Imaging Techniques," Pharmacotherapy, 1993, 13(5), pp. 486-480.

Nobrega, et al., "Resting and Reflex Heart Rate Responses During Cholinergic Stimulation With Pyridostigmine in Humans," Brazilin J. Med. Biol. Res, vol. 29, No. 11, pp. 1461-1465, 1996 (Abstract Only).

Noonan, David, "And the Beat Goes on," *Newsweek* , Jul. 11, 2005, pp. 56-57.

Okazawa, M., et al., "Effect of Vagal Stimulations and Parenteral Acetylcholine on Canine Trachealis Muscle Shortening," J. Appl. Physiol., vol. 72, No.6, pp. 2463-2468, 1992 (Abstract Only).

Penry, J. Kiffin, et al., "Prevention of Intractable Partial Seizures by Intermittent Vagal Stimulation in Humans: Preliminary Results," Epilepsia, 31(Suppl. 2), 1990, pp. S40-S43, Raven Press, Ltd., New York.

Pfister, et al., "Coronary Artery Bypass Without Cariopulmonary Bypass," Ann. Thorac. Surg., 54:1085-92.

Randall, Walter C., PhD., "Parasympathetic Control of the Heart," Chapter 4, Nervous Control of Cardiovascular Function, 1984, pp. 68-94.

Randall, Walter C., Ph.D. et al., "Functional Anatomy of the Cardiac Efferent Innervation," Neurocardiology, 1988, pp. 3-24.

Reid, Steven A., "Surgical Tecnique for Implantation of the Neurocybernetic Prosthesis," Epilepsia, 1990, 31(supp. 2) : S38-S39.

Rutecki, Paul, "Anatomical, Physiological, and Theoretical Basis for the Antiepileptic Effect of Vagus Nerve Stimulation," Epilepsia, 31(Suppl. 2), 1990, 1990, pp. S1-S6, Raven Press, Ltd., New York.

Subramanian, V.A., "Clinical Experience with Minimally Invasive Reoperative Coronary Bypass Surgery," Eur. J Cardio-Thorac Surg, 1996, 10:1058-1062.

Taylor, P., "Anticholinesterase Agents" Goodman and Gilman's, The Pharmacological Basis of Therapeutics, 6th Ed., MacMillan Publishing Co., Inc., New York, pp. 93-94 and 104-108, 1980.

Terry, Reese, et al., "An Implantable Neurocybernetic Prosthesis System," Epilepsia, 31 (Suppl. 2) 1990, pp. S33-S37, Raven Press, Ltd. New York.

Thompson, et al., "Bradycardia Induced by Intravascular Versus Direct Stimulation of the Vagus Nerve," Ann. Thorac. Surg., 1998; 65:637-42.

Urthaler, James f., "Experimental Studies on the Pathogenesis of Asystole After Verapamil in the Dog," am. J. cardiol., vol. 44, No. 4, pp. 651-656, 1979 (Abstract Only).

Uthman, Basim M., et al., "Efficacy and Safety of Vagus Nerve Stimulation in Patients with Complex Partial Seizures," Epilepsia, 31(Suppl. 2), 1990, pp. S44-S50, Raven Press, Ltd., New York.

Westaby, S., "Coronary Surgery Without Cardiopulmonary Bypass," British Heart Journal, 73:203-205.

Wilder, B.J., et al., "Vagus Nerve Stimulation for the Control of Epilepsy," Proceedings of a Symposium held in conjunction with the American Epilepsy Society Annual Meeting, Boston, MA, Dec. 2, 1989, vol. 31, Supplement 2, 1990.

Woodbury, Dixon M., et al., "Effects of Vagal Stimulation on Experimentally Induced Seizures in Rats," Epilepsia,31(Suppl. 2), 1990, pp. S7-S19, Raven Press, Ltd., New York.

US 6,184,239, 02/2001, Puskas (withdrawn)

* cited by examiner

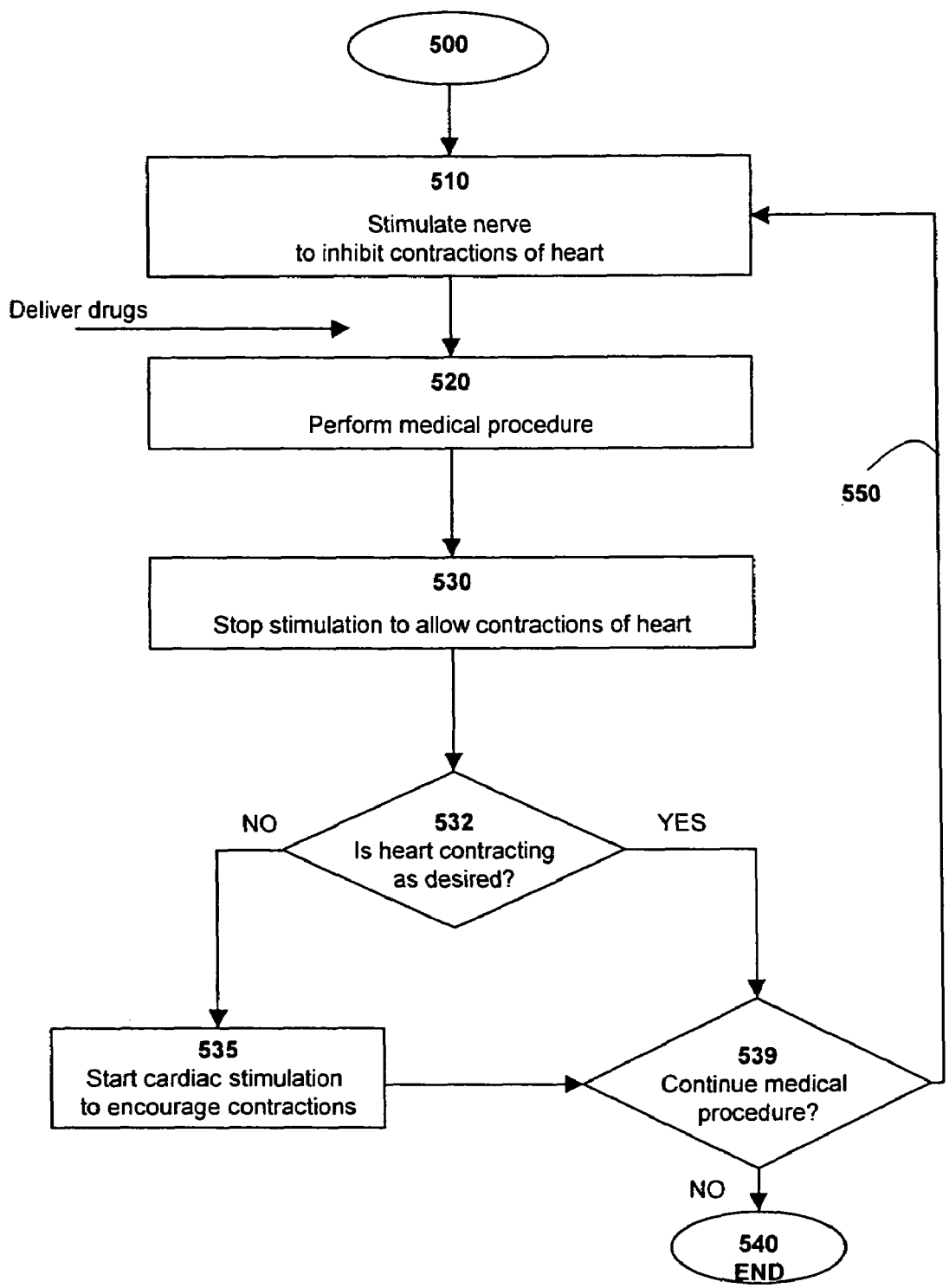

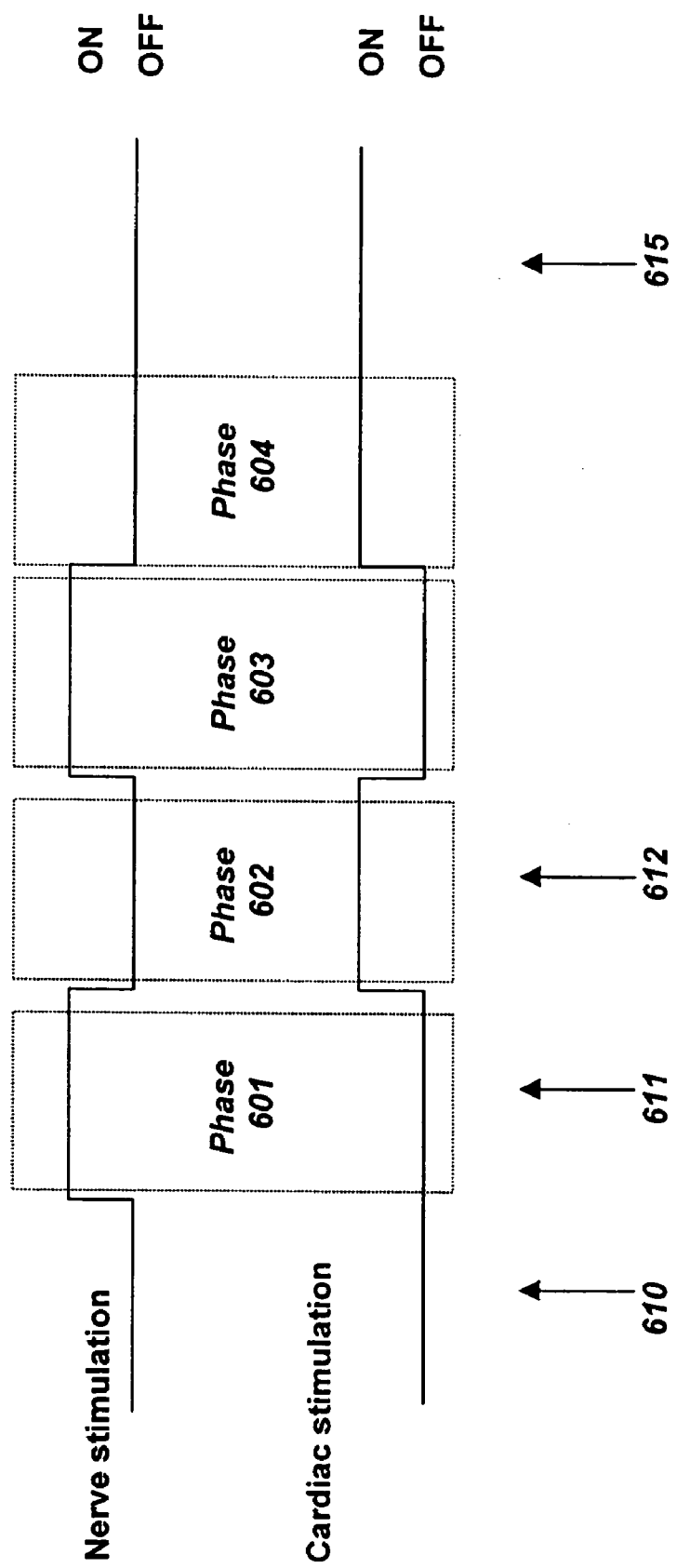

METHOD AND SYSTEM FOR NERVE STIMULATION PRIOR TO AND DURING A MEDICAL PROCEDURE

CROSS-REFERENCE TO RELATED APPLICATIONS

This application is a continuation of U.S. patent application Ser. No. 10/207,725, filed on Jul. 29, 2002, now U.S. Pat. No. 6,718,208 to inventors Hill, Jahns and Keogh, which is a continuation of U.S. patent application Ser. No. 09/670,441, filed on Sep. 26, 2000, now U.S. Pat. No. 6,449,507, to inventors Hill, Jahns and Keogh, which is a continuation-in-part of U.S. patent application Ser. No. 09/433,323, filed on Nov. 3, 1999, now U.S. Pat. No. 6,266,564, to inventors Hill and Jonkman, which is a continuation of U.S. patent application Ser. No. 09/070,506, filed on Apr. 30, 1998, now U.S. Pat. No. 6,006,134, to inventors Hill and Jonkman, which is a continuation-in-part of U.S. patent application Ser. No. 08/640,013, filed on Apr. 30, 1996, now abandoned.

FIELD OF THE INVENTION

This invention relates to methods for performing a medical procedure, especially a procedure during which it is necessary to adjust the beating of the heart. More particularly, this invention relates to methods and systems of stimulating a nerve in order to modify the beating of a heart to allow a medical procedure to be performed or for blood flow to be controlled.

BACKGROUND OF THE INVENTION

The current leading cause of death in the United States is coronary artery disease in which the coronary arteries are blocked by atherosclerotic plaques or deposits of fat. The typical treatment to relieve a partially or fully blocked coronary artery is coronary artery bypass graph (CABG) surgery.

CABG surgery, also known as "heart bypass" surgery, generally entails using a graph to bypass the coronary obstruction. The procedure is generally lengthy, traumatic and subject to patient risks. Among the risk factors involved is the use of a cardiopulmonary bypass (CPB) circuit, also known as a "heart-lung machine," to pump blood and oxygenate the blood so that the patient's heart may be stopped during the surgery.

Conventional CABG procedures are typically conducted on a stopped heart while the patient is on a (CPB) circuit. A stopped heart and a CPB circuit enables a surgeon to work in a bloodless, still operative field. However, there are a number of problems associated with CABG procedures performed while on CPB including the initiation of a systemic inflammatory response due to interactions of blood elements with the artificial material surfaces of the CPB circuit and global myocardial ischemia due to cardioplegic cardiac arrest. For these reasons, avoiding the use of CPB or cardioplegic cardiac arrest may help minimize post-operative complications.

One method, as disclosed in U.S. Pat. No. 5,651,378 to inventors Matheny and Taylor and in U.S. Pat. No. 5,913,876 to inventors Taylor et al., for facilitating coronary bypass surgery on a beating heart and thereby avoid the use of CPB and cardioplegic cardiac arrest includes stimulating the vagal nerve electrically in order to temporarily stop or substantially reduce the beating of the heart. This may be followed by pacing the heart to start its beating.

Another method, as disclosed in two published PCT applications, WO 99/09971 and WO 99/09973, both to inventor Puskas, involves stopping the beating of the heart during coronary bypass surgery using electrical stimulation of the vagal nerve in combination with administration of drugs. Another method, as disclosed in U.S. Pat. No. 6,060,454 to inventor Duhaylongsod, involves stopping the beating of the heart during coronary bypass surgery via the local delivery of drugs to the heart.

Although it is desirable to stop the heart for a period of time in order to allow the surgeon to accomplish a required task without interference from heart movement, i.e. a motionless operative field, it is undesirable to have the heart stopped for too long a period of time since the body needs, among other things, a constant supply of oxygen. In fact, it is particularly important to maintain sufficient blood flow, and therefore oxygen flow, to the brain. Stopping the heart for prolonged periods of time may cause damage to the patient.

It would be desirable therefore to provide a method for controllably stopping or slowing the heart intermittently for diagnostic purposes.

Additionally, it would be desirable to provide a method for controllably stopping or slowing the heart intermittently for therapeutic purposes.

Additionally, it would be desirable to provide a method for controllably stopping or slowing the heart intermittently in order to control blood flow.

Additionally, it would be desirable to provide a method for controllably stopping or slowing the heart intermittently in order to perform a medical procedure on the heart or another organ.

SUMMARY OF THE INVENTION

One aspect of the present invention provides a method of performing a medical procedure. The method includes stimulating a nerve to adjust the beating of a heart to a first condition. A medical procedure is then performed the medical procedure on an organ. Stimulation of the nerve is then reduced to adjust the beating of a heart to a second condition. The nerve is then stimulated a subsequent time in order to re-adjust the beating of the heart to the first condition and then the medical procedure is continued.

The nerve may be stimulated using transvascular stimulation. The stimulation may be stopped to achieve the second condition. The first condition may be a stopped or a slowed condition. The second condition may be a beating condition. The heart may also be stimulated to adjust the beating of the heart to the second condition. The heart may be stimulated by pacing.

Drugs, such as a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine, may be delivered during the medical procedure. These drugs may be naturally occurring or chemically synthesized.

The nerve being stimulated may be vagus nerve fibers, hypoglossal nerve fibers, phrenic nerve fibers, parasympathetic nerve fibers, and sympathetic nerve fibers, a vagal nerve, a carotid sinus nerve, a fat pad. The organ may be the heart.

The medical procedure may be surgical procedures, non-surgical procedures, endoscopic procedures, fluoroscopic procedures, stent delivery procedures, aortic aneurysm repairs, cranial aneurysm repairs, delivery of drugs, delivery of biological agents, cardiac surgery with cardiopulmonary bypass circuits, cardiac surgery without cardiopulmonary bypass circuits, brain surgery, cardiograms, heart valve repair, heart valve replacement, MAZE procedures, trans-myocardial revascularization, CABG procedures, beating heart surgery, vascular surgery, neurosurgery, electrophysiology procedures, diagnostic ablation of arrhythmias, therapeutic ablation of arrhythmias, endovascular procedures, treatment of injuries to the liver, treatment of the spleen, treatment of the heart, treatment of the lungs, treatment of major blood vessels, non-invasive procedures, invasive procedures, and port-access procedures.

Another aspect of the present invention provides a system for performing a medical procedure. The system includes a transvenous nerve stimulator to inhibit beating of the heart and a cardiac stimulator in communication with the transvenous nerve stimulator to stimulate beating of the heart. The system may also include drug delivery means for delivering at least one drug during the medical procedure such as a spray, a cream, an ointment, a medicament, a pill, a patch, a catheter, a cannula, a needle and syringe, a pump, and an iontophoretic drug delivery device. The transvenous nerve stimulator may stimulate vagus nerve fibers, hypoglossal nerve fibers, phrenic nerve fibers, parasympathetic nerve fibers, and sympathetic nerve fibers, a vagal nerve, a carotid sinus nerve, a fat pad. The transvenous nerve stimulator comprises one or more electrodes such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes and probe electrodes. The cardiac stimulator also comprises one or more electrodes such as cardiac stimulation electrodes, clip electrodes, needle electrodes, probe electrodes, pacing electrodes, epicardial electrodes, patch electrodes, intravascular electrodes, balloon-type electrodes, basket-type electrodes, tape-type electrodes, umbrella-type electrodes, suction-type electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. The system may also include a respiratory controller for controlling respiration.

Another aspect of the present invention provides a method of performing heart surgery. A nerve is stimulated transvenously to reduce the beating of a heart. The heart is operated upon. Stimulation of the nerve is then reduced or stopped. The heart is stimulated to cause beating of the heart. The nerve is then restimulated to re-inhibit beating of the heart and surgery is continued.

Another aspect of the present invention provides a device for performing a medical procedure. The device includes a processor connected to a transvenous nerve stimulation electrode and a cardiac stimulation electrode. The processor processes output from the nerve stimulation electrode and adjusts output from the cardiac stimulation electrode based on output from the nerve stimulation electrode. Stimulation from the nerve stimulation electrode may occur in an inverse relationship to stimulation from the cardiac stimulation electrode.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

BRIEF DESCRIPTION OF THE DRAWINGS

FIG. 3 is a flow diagram of one embodiment of a method of performing a medical procedure in accordance with the present invention; and FIG. 4 is a timeline view of one embodiment of a system for controllably stopping or slowing the heart intermittently in a patient monitoring blood flow in the brain during a medical procedure in accordance with the present invention.

DETAILED DESCRIPTION OF THE PRESENTLY PREFERRED EMBODIMENTS

Figure 1:
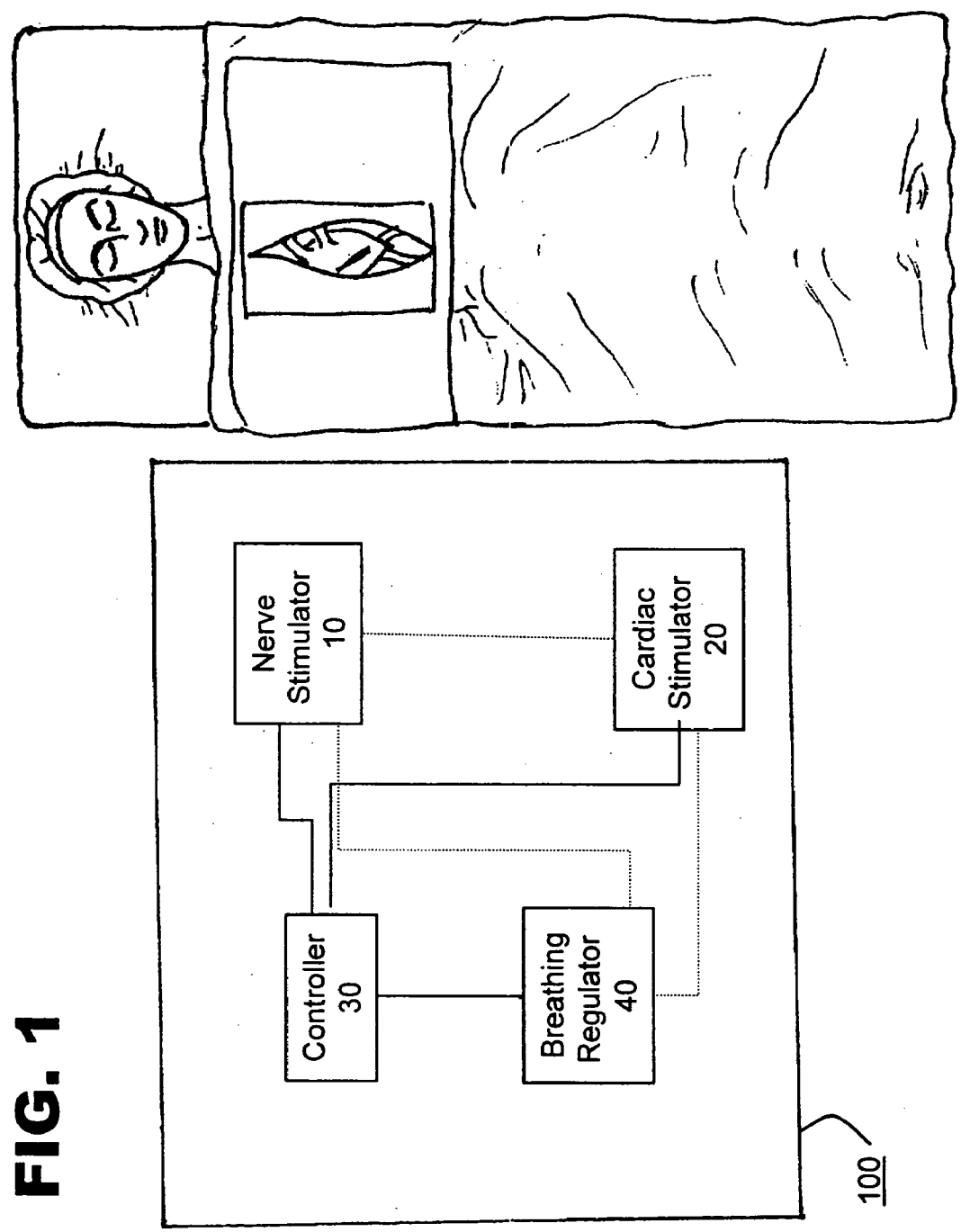
FIG. 1 is a schematic view of one embodiment of a system for performing a medical procedure in accordance with the present invention.

FIG. 1 shows a schematic view of one embodiment of a system for performing a medical procedure in accordance with the present invention at 100. System 100 comprises a nerve stimulator 10, and a cardiac stimulator 20. System 100 may also feature a controller 30 and a breathing regulator 40.

System 100 may also include a nerve stimulator 10. In one embodiment, the nerve stimulator 10 may be used to electrically manipulate cardiac rhythm by stimulating the vagus nerve. This vagal stimulation may produce asystole (slowing or stopping of the heart's beating.) Once this induced asystole is stopped, i.e. once the vagal stimulation is stopped, the heart may be allowed to return to its usual cardiac rhythm. Alternatively, the heart may be paced with an electrical pacing system, thereby maintaining a normal cardiac output. Vagal stimulation, alone or in combination with electrical pacing, may be used selectively and intermittently to allow a surgeon to perform a medical procedure during intermittent periods of asystole.

It is known that stimulation of the vagus nerve can reduce the sinus rate, as well as prolong AV conduction time or, if stimulation energies are high enough, induce AV node block. Use of vagal nerve stimulation to treat supraventricular arrhythmias and angina pectoris is disclosed in the article "Vagal Tuning" by Bilgutay et al., Journal of Thoracic and Cardiovascular Surgery, Vol. 56, No. 1, July, 1968, pp. 71–82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in California Medicine, Vol. 112, pp. 41–50, March, 1970.

As set forth in "Functional Anatomy of the Cardiac Efferent Innervation" by Randall et al., in Neurocardiology, edited by Kulbertus et al, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node", Bluemel et al., Am. J. Physiol. 259, (Heart Circ. Physiol. 28) H1504–H1510, 1990, stimulation of the fat pad associated with the SA node results in slowing of the sinus rate without the accompanying prolongation of AV conduction time which normally results from vagal nerve stimulation. The article also indicates that stimulation of the fat pad associated with the AV node is believed to produce corresponding effects limited to the AV node, i.e., extension of the AV conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, January, 1980, pp. 48–57, the fat pads associated with both the AV node and the SA node may be stimulated by means of electrodes located in the right pulmonary artery. The results obtained include both a depression of the sinus rate and a prolongation of the AV conduction time in response to continuous stimulation at 2–80 Hz at up to 50 ma.

Generally in healthy individuals, the SA node functions as the pacemaker. Normal heart rhythm associated with the SA node is typically referred to as sinus rhythm. When the SA node fails, the AV node generally takes over creating a heart rate of approximately 35 to 60 beats per minute. Heart rhythm associated with the AV node is typically referred to as nodal rhythm. When the AV node itself is blocked or injured, a new even slower pacemaker site may form at the junction of the AV node and the His bundle. Heart rhythm associated with this junction is typically referred to as junctional escape rhythm. When this junction site is inhibited, the Purkinje fibers in the His bundle or below may act as a pacemaker creating a heart rate of approximately 30 beats per minute. Heart rhythm associated with the Purkinje fibers is typically referred to as idioventricular rhythm.

In one embodiment of the present invention, nerve stimulator 10 may be used to electrically manipulate cardiac rhythm by stimulating the carotid sinus nerve, the fat pad associated with the SA node, the fat pad associated with the AV node, the junction of the AV node and the His bundle and/or the Purkinje fibers.

In one embodiment of the present invention, nerve stimulator 10 is used alone or in combination with other heart rate inhibiting agents to temporarily stop or slow the beating heart, thereby eliminating or reducing heart motion and/or blood flow during a medical procedure. For example, the present invention may be used to eliminate or reduce motion in the anastomosis field during CABG procedures such that a facilitated anastomosis procedure may be performed safely and effectively. The number of occasions that the vagal nerve may be stimulated depends on the type of medical procedure to be performed. Likewise, the type of medical procedure to be performed will dictate the duration of the individual electrical stimulations.

Nerve stimulator 10 may be powered by AC current, DC current or it may be battery powered either by a disposable or re-chargeable battery. Nerve stimulator 10 may be configured to synchronize activation and deactivation of breathing regulator 40 with vagal stimulation, thereby minimizing or eliminating unwanted heart and chest motion associated with the patient's breathing. Nerve stimulator 10 may comprise a surgeon controlled switch box. A switch may be incorporated in or on one of the surgeon's instruments, such as surgical site retractor, or any other location easily and quickly accessed by the surgeon for regulation of the nerve stimulator 10 by the surgeon. The switch may be, for example, a hand switch, a foot switch, or a voice-activated switch comprising voice-recognition technologies.

A visual and/or audible signal used to alert a surgeon to the completion or resumption of vagal nerve stimulation may be incorporated into nerve stimulator 10. For example, a beeping tone or flashing light that increases in frequency as the nerve stimulation period should end or begin may be used.

Nerve stimulator 10 may be slaved to cardiac stimulator 20 or cardiac stimulator 20 may be slaved to nerve stimulator 10. For example, the output of cardiac stimulator 20 may be off whenever the output of nerve stimulator 10 is on. Software controlling cardiac stimulator 20 may be designed to automatically commence cardiac pacing if the heart does not resume beating within a pre-determined interval after cessation of vagal nerve stimulation. In addition, the software controlling nerve stimulator 10 may be designed to automatically stop vagal nerve stimulation if the heart has been stopped for too long.

System 100 may also include cardiac stimulator 20 which may be used to stimulate the heart as desired. As with nerve stimulator 10, cardiac stimulator 20 may be intermittently stopped and started to allow the surgeon to perform individual steps of a medical procedure.

Cardiac stimulator 20 may be a conventional ventricular demand pacer or dual chamber (atrial-ventricular) pacer. Cardiac stimulator 20 may be powered by AC current, DC current or it may be battery powered either by a disposable or re-chargeable battery. Cardiac stimulator 20 may be configured to synchronize activation and deactivation of breathing regulator 40 with pacing, thereby minimizing or eliminating unwanted heart and chest motion associated with the patient's breathing. Cardiac stimulator 20 may be any conventional pacing device suitable for ventricular demand pacing and having leads electrically coupled to a switch box. Cardiac stimulator 20 may be combined in a single unit with a switch box. Cardiac stimulator 20 may comprise a surgeon controlled switch box. A switch may be incorporated in or on one of the surgeon's instruments, such as surgical site retractor, or any other location easily and quickly accessed by the surgeon for regulation of the cardiac stimulator by the surgeon. The switch may be, for example, a hand switch, a foot switch, or a voice-activated switch comprising voice-recognition technologies. A single switch may be used to regulate both cardiac stimulator 20 and nerve stimulator 10.

A visual and/or audible signal used to prepare a surgeon for the resumption of pacing may be incorporated into cardiac stimulator 20. For example, a beeping tone or flashing light that increases in frequency as the pacing period ends may be used. A single signaling method or device may be used for both cardiac stimulator 20 and nerve stimulator 10.

Nerve stimulator 10 and/or cardiac stimulator 20 may be slaved to a robotic system or a robotic system may be slaved to nerve stimulator 10 and/or cardiac stimulator 20. Breathing regulator 40 and other components may also be slaved to such a system. Computer- and voice-controlled robotic systems that position and maneuver endoscopes and/or other surgical instruments for performing microsurgical procedures such as anastomoses through small incisions may be used by a surgeon to perform precise and delicate maneuvers. These robotic systems may allow a surgeon to perform a variety of microsurgical procedures including endoscopic CABG. Endoscopic CABG may allow multiple occluded coronary arteries to be bypassed without a thoracotomy or mini-thoracotomy. Heart valve repair and replacement may also be other surgical applications for these robotic systems. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

System 100 may also include a breathing regulator 40. In one embodiment, the breathing regulator 40 may be used to stimulate the phrenic nerve in order to provide a diaphragmatic pacemaker. Breathing regulator 40 may comprise one or more electrodes for supplying electrical current to the phrenic nerve to control breathing during vagal and/or cardiac stimulation and/or destimulation. Electrodes used to stimulate the phrenic nerve may be, for example, non-invasive, e.g., clips, or invasive, e.g., needles or probes. The application of an electrical stimulus to the phrenic nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision, placed on the skin or in combinations thereof. The present invention may include various electrodes, catheters and electrode catheters suitable for phrenic nerve stimulation to control breathing.

Phrenic nerve stimulation electrodes may be intravascular, patch-type, balloon-type, basket-type, umbrella-type, tape-type, cuff-type, suction-type, screw-type, barb-type, bipolar, monopolar, metal, wire, endotracheal, endoesophageal, intravascular, transcutaneous or intracutaneous electrodes. Guided or steerable catheter devices comprising electrodes may be used alone or in combination with the nerve stimulation electrodes. For example, a catheter comprising one or more wire, metal strips or metal foil electrodes or electrode arrays may be used. The catheter may comprise, for example, a balloon which may be inflated with air or liquid to press the electrodes firmly against a vessel wall that lays adjacent the phrenic nerve.

Phrenic nerve stimulation electrodes may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters which incorporate one or more tunnels or passageways.

In another embodiment, the breathing regulator 40 may comprise a connector which interfaces with a patient's respirator, and sends a logic signal to activate or deactivate the respirator to control breathing during vagal and/or cardiac stimulation and/or destimulation.

Figure 2:
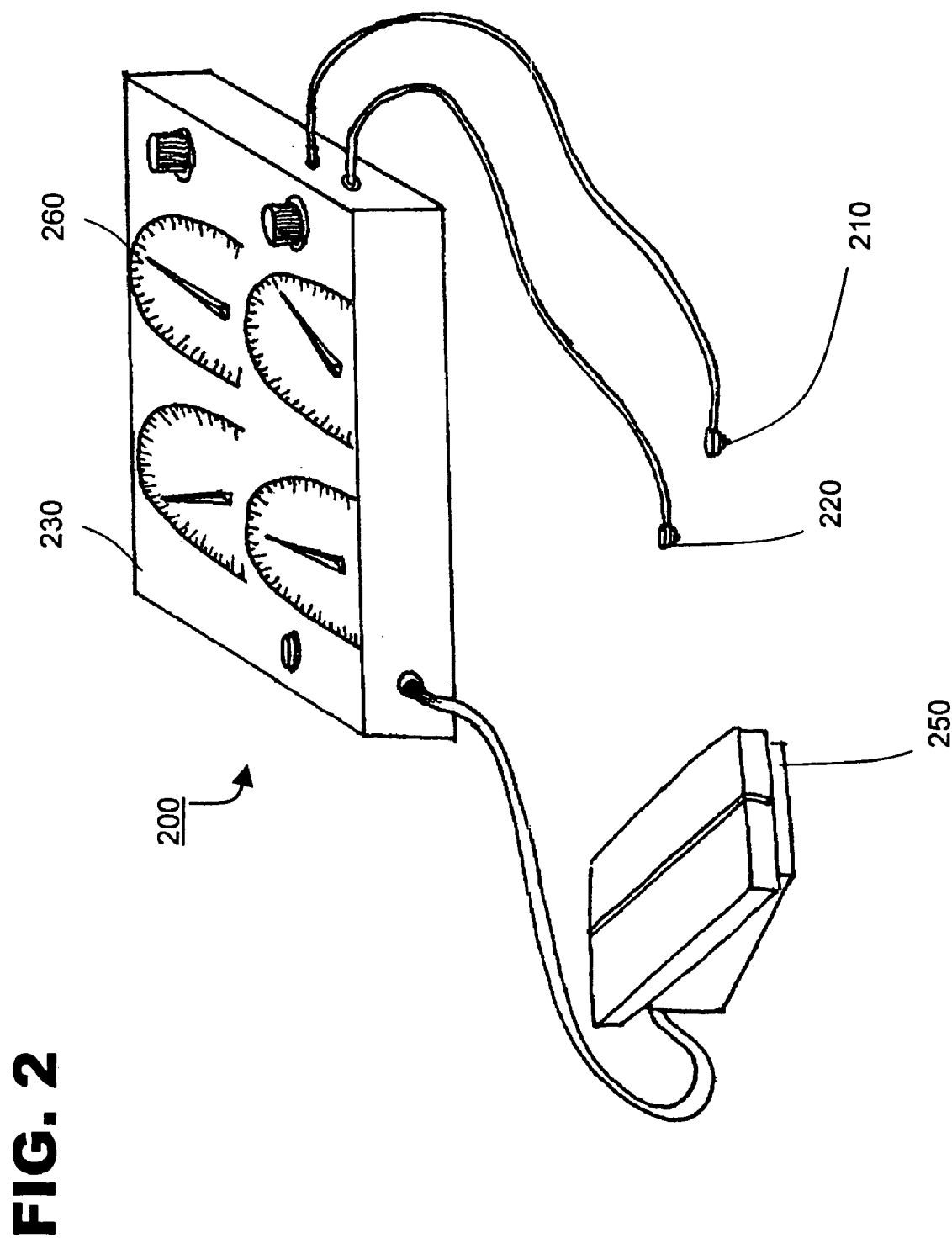
FIG. 2 is a schematic view of one embodiment of a medical device in accordance with the present invention.

FIG. 2 shows one embodiment of the present invention at 200. In this embodiment, the elements named above may be combined or connected to a control unit along with other components. The unit 200 may be used to coordinate the various elements. Unit 200 may incorporate a controller or any suitable processor 230.

Unit 200 may incorporate a nerve stimulator. For example, FIG. 2 shows an electrode for nerve stimulation at 210. Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes 210 may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present invention may include various electrodes, catheters and electrode catheters suitable for vagal nerve stimulation to temporarily stop or slow the beating heart alone or in combination with other heart rate inhibiting agents.

Nerve stimulation electrodes 210 may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes 210. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon which may be inflated with air or liquid to press the electrodes firmly against the vessel wall. Similar techniques may be performed by insertion of a catheter-type device into the trachea or esophagus. Additionally, tracheal tubes and esophageal tubes comprising electrodes may be used.

Nerve stimulation electrodes 210 may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters which incorporate one or more tunnels or passageways.

In one embodiment of the present invention, the location of the electrodes 210 is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues.

Unit 200 may also incorporate a cardiac stimulator. For example, FIG. 2 shows an electrode for stimulation of the heart at 220. Cardiac electrodes 220 used to stimulate the heart may be, for example, non-invasive, e.g., clips, or invasive, e.g., needles or probes. Electrodes 220 may be positioned through a thoracotomy, sternotomy, endoscopically through a percutaneous port, through a stab wound or puncture, through a small incision in the chest, placed on the chest or in combinations thereof. The present invention may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes.

Controller 230 may be used to gather information from nerve stimulation electrodes 210 and cardiac stimulation electrodes 220. Controller 230 may also be used to control the stimulation levels and stimulation duration of nerve stimulation electrodes 210 and cardiac stimulation electrodes 220. Controller 230 may also gather and process information from the various components of system 100. This information may be used to adjust stimulation levels and stimulation times of nerve stimulation electrodes 210 and cardiac stimulation electrodes 220.

Unit 200 may incorporate one or more switches to facilitate regulation of the various components by the surgeon. One example of such a switch is shown as foot pedal 250. The switch may also be, for example, a hand switch, or a voice-activated switch comprising voice-recognition technologies. The switch may be incorporated in or on one of the surgeon's instruments, such as surgical site retractor, or any other location easily and quickly accessed by the surgeon.

Unit 200 may also include a display 260. Unit 200 may also include other means of indicating the status of various components to the surgeon such as a numerical display, gauges, a monitor display or audio feedback. Unit 200 may also include one or more visual and/or audible signals used to prepare a surgeon for the start or stop of nerve stimulation and/or cardiac stimulation.

FIG. 3 shows a flow diagram of one embodiment of the present invention. The patient is prepared for a medical procedure at 500.

At block 510, a nerve that controls the beating of the heart is stimulated. Such a nerve may be for example a vagal nerve. The nerve may be stimulated to slow, inhibit or stop the contractions of the heart.

Also at block 510, one or more of a variety of pharmacological agents or drugs may be delivered. These drugs may produce reversible asystole of a heart while maintaining the ability of the heart to be electrically paced.

A variety of pharmacological agents or drugs may also be delivered at other times during the procedure 500. These drugs may also produce reversible asystole of a heart while maintaining the ability of the heart to be electrically paced. Other drugs may be administered for a variety of functions and purposes as described below. Drugs may be delivered at any appropriate time during the medical procedure, for example, at the beginning of the procedure, intermittently during the procedure, continuously during the procedure, or following the procedure.

Drugs, drug formulations or compositions suitable for administration to a patient during a medical procedure may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

Drugs may be delivered via a drug delivery device that may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques.

Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed.

The negative electrode would contact the heart or other body part at some desired distance point to complete the circuit. One or more of the electrodes may also be used as nerve stimulation electrodes 210 or as cardiac stimulation electrodes 220.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential. The present invention may be combined with conventional CPB, the induced asystole as described by this invention may serve as a substitute for conventional cardioplegic arrest. For example, the combination of drugs and vagal stimulation may be used as a cardioplegic agent in a variety of medical procedures.

Drugs, drug formulations and/or drug compositions that may be used during according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

In one embodiment, the cardiac asystole produced in accordance with the present invention is reversible, e.g., chemically such as by the administration of atropine or by natural forces. Beta-adrenergic stimulation or administration of calcium solutions may be used to reverse the effects of a calcium channel blocker such as verapamil. Agents that promote heart rate and/or contraction may be used in a preferred embodiment of the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

Typically, vagal nerve stimulation prevents the heart from contracting. This non-contraction must then be followed by periods without vagal nerve stimulation during which the heart is allowed to contract.

At Block 520, a medical procedure may be performed or begun. Such a procedure may be, for example, surgery on the heart. Alternatively, the procedure may be surgery performed on another organ of the body.

The term "medical procedure" may mean any one or more medical or surgical procedures such as, for example cardiac surgery, performed with or without cardiopulmonary bypass (CPB) circuits, heart valve repair, heart valve replacement, MAZE procedures, revascularization procedures, transmyocardial revascularization (TMR) procedures, percutaneous myocardial revascularization (PMR) procedures, CABG procedures, anastomosis procedures, non-surgical procedures, fluoroscopic procedures, beating heart surgery, vascular surgery, neurosurgery, brain surgery, electrophysiology procedures, diagnostic and therapeutic procedures, ablation procedures, ablation of arrhythmias, endovascular procedures, treatment of the liver, spleen, heart, lungs, and major blood vessels, aneurysm repair, imaging procedures of the heart and great vessels, CAT scans or MRI procedures, pharmacological therapies, drug delivery procedures, gene therapies, cellular therapies, cancer therapies, radiation therapies, genetic, cellular, tissue and/or organ manipulation or transplantation procedures, coronary angioplasty procedures, placement or delivery of coated or noncoated stents, atherectomy procedures, atherosclerotic plaque manipulation and/or removal procedures, procedures where bleeding needs to be precisely controlled, procedures that require precise control of cardiac motion and/or bleeding.

When the medical procedure comprises one or more medical devices, e.g., coated stents, these devices may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized.

The medical procedure may be non-invasive, minimally invasive and/or invasive. The medical procedure may entail a port-access approach, a partially or totally endoscopic approach, a sternotomy approach or a thoracotomy approach. The medical procedure may include the use of various mechanical stabilization devices or techniques as well as various robotic or imaging systems.

In one method, the heart may be temporarily slowed or intermittently stopped for short periods of time to permit the surgeon to accomplish the required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers," Dec. 21, 1999, to inventors Hill and Junkman. This patent is assigned to Medtronic, Inc. and is incorporated herein by reference.

After a time, the medical procedure or one phase of the medical procedure is completed at 520. As seen at Block 530, after all or some phase of the medical procedure is performed, cardiac contractions are allowed to occur. Cardiac contractions may be allowed to occur intermittently during the procedure to ensure adequate blood flow. In one embodiment, the stimulation from the nerve stimulator 10 is stopped or slowed enough to allow the heart to contract. For example, the vagal nerve stimulation is removed, thereby allowing cardiac contractions to occur.

As seen at Block 532, it may be evaluated if the cardiac contractions are occurring as desired.

As seen at Block 535, if the contractions are not occur as desired, the heart may be stimulated to ensure that cardiac contractions occur. For example, cardiac stimulator 20 may be used to apply pacing pulses to the heart to encourage the heart to contract normally. In particular, the pacing pulses may be applied to the ventricle as is well known in the field. Once the heart is contracting as desired, the method may proceed to Block 539.

The present invention permits the heat to be stilled for selected and controllable periods of time in order to permit cardiac or other medical procedure to be performed. While such a period of stillness is desired, it must not last too long, otherwise insufficient blood and oxygen is delivered to organs. Thus, it is necessary to have the periods when the heart is beating (by stopping stimulation to allow contractions as seen at Block 530 and/or by starting cardiac stimulation to encourage contractions as seen at Block 535).

As seen at Block 539, if the heart is contracting as desired, it may be determined if additional medical procedures or additional stages of the current medical procedure need to be performed. If not, the method may end as seen at Block 540. If it is determined that the procedure should continue, the heart may again be stilled using the methods of stilling the heart described above. Thus, as seen at 550, the method of the present invention may return to Block 510 and be repeated. For example, the heart may again be prevented from contracting by stimulation of the vagal nerve (Block 510). Additional drugs may be delivered or the drugs previously administered may continue to be administered.

Additional surgery, additional steps in the medical procedure or additional medical procedures may again be performed (Block 520) while the heart is still. Then, this stage of stillness may be followed by another stage when the stimulation is removed (Block 530) and the heart is allowed to contract. Again, the heart may be stimulated to encourage contractions (Block 535).

This cycle may be repeated until the procedure, such as the surgery, is completed. After the procedure is completed, step 535 may be performed until the heart is beating normally. At the procedure's end, one or more of a variety of pharmacological agents or drugs may be delivered or may continue to be delivered for example to alleviate pain or aid in recuperation. Other drugs may be administered for a variety of functions and purposes as described above.

For example, a surgical procedure at 520 may require several stitches to be made by the surgeon. The surgeon may stimulate the vagal nerve at 510 to stop the heart. Then the surgeon may make the first stitch at 520. The surgeon may then reduce or halt stimulation at 530 and allow the heart to contract. The surgeon may also pace the heart at 535. Then at 540, the surgeon may return to 510 to inhibit contractions of the heart. At 520, the surgeon will then make the second stitch. This process may be repeated (the loop designated by 540 may be repeated) until all the required stitches have been made.

FIG. 4 is a timeline showing the relation of the vagal nerve stimulation to the cardiac stimulation in one embodiment of the present invention.

Point 610 indicates a point before the medical procedure has begun. At this point 610, both nerve stimulation and cardiac stimulation are off. At point 610, the heart is beating regularly. Then nerve stimulation is turned on to inhibit beating of the heart. During phase 601, the vagal nerve stimulation is on and the cardiac stimulation is off. This is the condition of the two types of stimulation at step 520 described above. Point 611 is a representative point during phase 601. At point 611, the contractions of the heart are stilled or substantially slowed. Then during phase 602 the vagal stimulation is turned off (as described at step 530) and the cardiac stimulation may be turned on (as described at 535). Point 612 is a representative point during phase 602. At point 612, the contractions are allowed and/or may be induced. During phase 603, the vagal nerve stimulation is again turned on and the cardiac stimulation is turned off. Then during phase 604 the vagal stimulation is again turned off and the cardiac stimulation may again be turned on. The method of the present invention may be repeated as necessary until a point is reached, represented by point 615, when the necessary medical procedures are completed. At this point 615, nerve stimulation is off although cardiac stimulation may be left on in order to pace the heart to its normal rhythm.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method for controllably stopping or slowing a heart intermittently during a medical procedure, comprising:
    providing a controllable nerve stimulator capable of automatically stopping stimulation of a vagal nerve, the nerve stimulator comprising a nerve stimulation electrode;
    positioning the nerve stimulation electrode in a position suitable for stimulating a vagal nerve to stop or slow the heart;
    controllably starting stimulation of the vagal nerve; automatically stopping stimulation of the vagal nerve;
    continuing to start and stop stimulation of the vagal nerve in order to stop or slow the heart intermittently during the medical procedure.

2. The method of claim 1 wherein the vagal nerve is stimulated using transvascular stimulation.

3. The method of claim 1 wherein the vagal nerve is stimulated using endotracheal stimulation.

4. The method of claim 1 wherein the vagal nerve is stimulated using esophageal stimulation.

5. The method of claim 1 wherein the vagal nerve is stimulated using transcutaneous stimulation.

6. The method of claim 1 wherein the vagal nerve is stimulated using intracutaneous stimulation.

7. The method of claim 1 further comprising delivering at least one drug during the medical procedure.

8. The method of claim 7 wherein the drug is selected from the group consisting of: a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

9. The method of claim 7 wherein the drug is naturally occurring.

10. The method of claim 7 wherein the drug is chemically synthesized.

11. The method of claim 1 further comprising stimulating the heart.

12. The method of claim 11 wherein stimulation of the vagal nerve occurs in an inverse relationship to stimulation of the heart.

13. The method of claim 11 wherein the heart is stimulated by pacing.

14. The method of claim 1 wherein the medical procedure is selected from the group consisting of: surgical procedures, non-surgical procedures, endoscopic procedures, fluoroscopic procedures, stent delivery procedures, aortic aneurysm repairs, cranial aneurysm repairs, delivery of drugs, delivery of biological agents, cardiac surgery with cardiopulmonary bypass circuits, cardiac surgery without cardiopulmonary bypass circuits, brain surgery, cardiograms, heart valve repair, heart valve replacement, MAZE procedures, transmyocardial revascularization, CABG procedures, beating heart surgery, vascular surgery, neurosurgery, electrophysiology procedures, diagnostic ablation of arrhythmias, therapeutic ablation of arrhythmias, endovascular procedures, treatment of injuries to the liver, treatment of the spleen, treatment of the heart, treatment of the lungs, treatment of major blood vessels, non-invasive procedures, invasive procedures, and port-access procedures.

15. A method of performing a medical procedure, comprising:
    providing a nerve stimulator capable of automatically stopping stimulation of a vagal nerve;
    stimulating the vagal nerve to reduce heart rate;
    automatically stopping stimulation of the vagal nerve; and
    stimulating the vagal nerve a subsequent time in order to reduce heart rate a subsequent time.

16. The method of claim 15 wherein the vagal nerve is stimulated using transvascular stimulation.

17. The method of claim 15 wherein the vagal nerve is stimulated using endotracheal stimulation.

18. The method of claim 15 wherein the vagal nerve is stimulated using esophageal stimulation.

19. The method of claim 15 wherein the vagal nerve is stimulated using transcutaneous stimulation.

20. The method of claim 15 wherein the vagal nerve is stimulated using intracutaneous stimulation.

21. The method of claim 15 further comprising delivering at least one drug during the medical procedure.

22. The method of claim 21 wherein the drug is selected from the group consisting of: a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

23. The method of claim 21 wherein the drug is naturally occurring.

24. The method of claim 21 wherein the drug is chemically synthesized.

25. The method of claim 15 further comprising stimulating the heart.

26. The method of claim 25 wherein stimulation of the vagal nerve occurs in an inverse relationship to stimulation of the heart.

27. The method of claim 25 wherein the heart is stimulated by pacing.

28. The method of claim 25 wherein the medical procedure is selected from the group consisting of: surgical procedures, non-surgical procedures, endoscopic procedures, fluoroscopic procedures, stent delivery procedures, aortic aneurysm repairs, cranial aneurysm repairs, delivery of drugs, delivery of biological agents, cardiac surgery with cardiopulmonary bypass circuits, cardiac surgery without cardiopulmonary bypass circuits, brain surgery, cardiograms, heart valve repair, heart valve replacement, MAZE procedures, transmyocardial revascularization, CABG procedures, beating heart surgery, vascular surgery, neurosurgery, electrophysiology procedures, diagnostic ablation of arrhythmias, therapeutic ablation of arrhythmias, endovascular procedures, treatment of injuries to the liver, treatment of the spleen, treatment of the heart, treatment of the lungs, treatment of major blood vessels, non-invasive procedures, invasive procedures, and port-access procedures.

29. A method of electrically manipulating heart rhythm during therapeutic treatment of a heart, comprising:
providing a nerve stimulator, the nerve stimulator comprising a nerve stimulation electrode;
positioning the nerve stimulation electrode in a position suitable for electrically stimulating a vagal nerve to manipulate heart rhythm; and
intermittently starting and automatically stopping electrical stimulation of the vagal nerve subsequent times in order to manipulate heart rhythm during therapeutic treatment of the heart.

30. The method of claim 29 wherein the nerve stimulation electrode is positioned in a transvascular position.

31. The method of claim 29 wherein the nerve stimulation electrode is positioned in a transcutaneous position.

32. The method of claim 29 wherein the nerve stimulation electrode is positioned in an intracutaneous position.

33. The method of claim 29 further comprising delivering at least one drug during treatment of the heart.

34. The method of claim 33 wherein the drug is chemically synthesized.

35. The method of claim 29 further comprising stimulating the heart.

36. The method of claim 35 wherein stimulation of the vagal nerve occurs in an inverse relationship to stimulation of the heart.

37. The method of claim 35 wherein the heart is stimulated by pacing.

38. A method of electrically manipulating heart rhythm during therapeutic treatment of a heart, comprising:
providing a nerve stimulator, the nerve stimulator comprising a nerve stimulation electrode;
positioning the nerve stimulation electrode in a position suitable for electrically stimulating a vagal nerve to manipulate heart rhythm; and
intermittently starting and stopping electrical stimulation of the vagal nerve subsequent times in order to manipulate heart rhythm during therapeutic treatment of the heart;
the nerve stimulation electrode being positioned in an endotracheal position.

39. A method of electrically manipulating heart rhythm during therapeutic treatment of a heart, comprising:
providing a nerve stimulator, the nerve stimulator comprising a nerve stimulation electrode;
positioning the nerve stimulation electrode in a position suitable for electrically stimulating a vagal nerve to manipulate heart rhythm; and
intermittently starting and stopping electrical stimulation of the vagal nerve subsequent times in order to manipulate heart rhythm during therapeutic treatment of the heart;
the nerve stimulation electrode being positioned in an esophageal position.

40. A method of electrically manipulating heart rhythm during therapeutic treatment of a heart, comprising:
providing a nerve stimulator, the nerve stimulator comprising a nerve stimulation electrode;
positioning the nerve stimulation electrode in a position suitable for electrically stimulating a vagal nerve to manipulate heart rhythm;
intermittently starting and stopping electrical stimulation of the vagal nerve subsequent times in order to manipulate heart rhythm during therapeutic treatment of the heart; and
delivering at least one drug during treatment of the heart;
the drug being selected from the group consisting of: a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

41. A method of electrically manipulating heart rhythm during therapeutic treatment of a heart, comprising:
providing a nerve stimulator, the nerve stimulator comprising a nerve stimulation electrode;
positioning the nerve stimulation electrode in a position suitable for electrically stimulating a vagal nerve to manipulate heart rhythm;
intermittently starting and stopping electrical stimulation of the vagal nerve subsequent times in order to manipulate heart rhythm during therapeutic treatment of the heart; and
delivering at least one drug during treatment of the heart;
the drug being naturally occurring.

42. A method of electrically manipulating cardiac rhythm during a medical procedure, comprising:
providing a nerve stimulator, the nerve stimulator comprising a stimulation electrode;
positioning the stimulation electrode in a position suitable for stimulating a carotid sinus nerve to manipulate cardiac rhythm;
intermittently starting and stopping stimulation of the carotid sinus nerve multiple times in order to manipulate cardiac rhythm during a medical procedure.

43. A method of electrically manipulating cardiac rhythm during a medical procedure, comprising:
providing a stimulator, the stimulator comprising a stimulation electrode;
positioning the stimulation electrode in a position suitable for stimulating Purkinje fibers to stop or slow cardiac rhythm;
intermittently starting and stopping stimulation of the Purkinje fibers multiple times in order to manipulate cardiac rhythm during a medical procedure.

44. A method of electrically manipulating cardiac rhythm during a medical procedure, comprising:
providing a stimulator, the stimulator comprising a stimulation electrode;
positioning the stimulation electrode in a position suitable for stimulating a junction of an AV node and a His bundle to manipulate cardiac rhythm;
intermittently starting and stopping stimulation of the junction of the AV node and the His bundle multiple times in order to manipulate cardiac rhythm during a medical procedure.

45. A method of electrically manipulating cardiac rhythm during a medical procedure, comprising:
- providing a stimulator, the stimulator comprising a stimulation electrode;
- positioning the stimulation electrode in a position suitable for stimulating a fat pad associated with AV node to manipulate cardiac rhythm; and
- intermittently starting and stopping stimulation of the fat pad associated with the AV node multiple times in order to manipulate cardiac rhythm during a medical procedure.

46. A method of electrically manipulating cardiac rhythm during a medical procedure, comprising:
- providing a stimulator, the stimulator comprising a stimulation electrode;
- positioning the stimulation electrode in a position suitable for stimulating a fat pad associated with a SA node to manipulate cardiac rhythm; and
- intermittently starting and stopping stimulation of the fat pad associated with the SA node multiple times in order to manipulate cardiac rhythm during a medical procedure.

* * * * *